(12) United States Patent
Trautman et al.

(10) Patent No.: US 9,387,315 B2
(45) Date of Patent: Jul. 12, 2016

(54) MICROPROTRUSION MEMBER RETAINER FOR IMPACT APPLICATOR

(71) Applicant: Alza Corporation, Vacaville, CA (US)

(72) Inventors: Joseph C. Trautman, Sunnyvale, CA (US); Richard L. Keenan, Saratoga, CA (US)

(73) Assignee: Alza Corporation, Vacaville, CA (US)

( * ) Notice: Subject to any disclaimer, the term of this patent is extended or adjusted under 35 U.S.C. 154(b) by 0 days.

(21) Appl. No.: 14/306,854

(22) Filed: Jun. 17, 2014

(65) Prior Publication Data

US 2014/0364801 A1     Dec. 11, 2014

Related U.S. Application Data

(60) Division of application No. 10/978,807, filed on Nov. 1, 2004, now Pat. No. 8,753,318, which is a continuation of application No. 09/976,762, filed on Oct. 12, 2001, now Pat. No. 6,855,131.

(60) Provisional application No. 60/240,379, filed on Oct. 13, 2000.

(51) Int. Cl.
*A61M 5/00*     (2006.01)
*A61M 37/00*    (2006.01)
*A61B 17/20*    (2006.01)
*A61B 17/00*    (2006.01)

(52) U.S. Cl.
CPC .......... *A61M 37/0015* (2013.01); *A61B 17/205* (2013.01); *A61B 2017/00747* (2013.01); *A61M 2037/0023* (2013.01); *A61M 2037/0046* (2013.01)

(58) Field of Classification Search
CPC .................. A61B 17/205; A61B 2017/00747; A61M 2037/0023; A61M 2037/0046; A61M 37/0015
USPC ........................................ 604/191, 500–522
See application file for complete search history.

(56) References Cited

U.S. PATENT DOCUMENTS 5,402,798 A * 4/1995 Swierczek ........... A61B 5/1411
                                                 600/583

* cited by examiner

*Primary Examiner* — Phillip Gray
(74) *Attorney, Agent, or Firm* — Sunstein Kann Murphy & Timbers LLP

(57) ABSTRACT

A retainer (34) is provided for holding a microprotrusion member (44) for application of the microprotrusion member (44) to the stratum corneum with an impact applicator (10). The microprotrusion member (44) includes a plurality of microprotrusions (90) which penetrate the stratum corneum to improve transport of an agent across the stratum corneum.

2 Claims, 10 Drawing Sheets

MICROPROTRUSION MEMBER RETAINER FOR IMPACT APPLICATOR

CROSS REFERENCE

This application is a Divisional Application of U.S. application Ser. No. 10/978,807, filed on Nov. 1, 2004, which was a Continuation Application of U.S. application Ser. No. 09/976,762, filed on Oct. 12, 2001, now U.S. Pat. No. 6,855,131, issued on Feb. 15, 2005, which claimed priority to U.S. Provisional Application 60/240,379, filed on Oct. 13, 2000, all of which are hereby incorporated by reference in the entirety.

TECHNICAL FIELD

The invention relates to an apparatus and method for applying a microprotrusion member to the stratum corneum by impact, and more particularly, the invention relates to a retainer for mounting a microprotrusion member having a plurality of microprotrusions on an impact applicator device to reproducibly penetrate the stratum corneum with microprotrusions.

BACKGROUND ART

Interest in the percutaneous or transdermal delivery of peptides and proteins to the human body continues to grow with the increasing number of medically useful peptides and proteins becoming available in large quantities and pure form. The transdermal delivery of peptides and proteins still faces significant problems. In many instances, the rate of delivery or flux of polypeptides through the skin is insufficient to produce a desired therapeutic effect due to their large size and molecular weight. In addition, polypeptides and proteins are easily degraded during and after penetration into the skin, prior reaching target cells. Likewise, the passive transdermal flux of many low molecular weight compounds is too limited to be therapeutically effective.

One method of increasing the transdermal delivery of agents relies on pretreating the skin with, or co-delivering with the beneficial agent, a skin permeation enhancer. A permeation enhancer substance, when applied to a body surface through which the agent is delivered, enhances the transdermal flux of the agent such as by increasing the permselectivity and/or permeability of the body surface, and/or reducing the degradation of the agent.

Another method of increasing the agent flux involves the application of an electric current across the body surface referred to as "electrotransport." "Electrotransport" refers generally to the passage of a beneficial agent, e.g., a drug or drug precursor, through a body surface, such as skin, mucous membranes, nails, and the like. The transport of the agent is induced or enhanced by the application of an electrical potential, which results in the application of electric current, which delivers or enhances delivery of the agent. Electrotransport delivery generally increases agent delivery and reduces polypeptide degradation during transdermal delivery.

There also have been many attempts to mechanically penetrate or disrupt the skin in order to enhance the transdermal flux, such as, U.S. Pat. No. 5,879,326 issued to Godshall, et al., U.S. Pat. No. 3,814,097 issued to Ganderton, et al., U.S. Pat. No. 5,279,544 issued to Gross, et al., U.S. Pat. No. 5,250,023 issued to Lee, et al., U.S. Pat. No. 3,964,482 issued to Gerstel, et al., Reissue 25,637 issued to Kravitz, et al., and PCT Publication Nos. WO 96/37155, WO 96/37256, WO 96/17648, WO 97/03718, WO 98/11937, WO 98/00193, WO 97/48440, WO 97/48441, WO 97/48442, WO 98/00193, WO 99/64580, WO 98/28037, WO 98/29298, and WO 98/29365. These devices use piercing elements or microprotrusions of various shapes and sizes to pierce the outermost layer (i.e., the stratum corneum) of the skin. The microprotrusions disclosed in these references generally extend perpendicularly from a thin, flat member, such as a pad or sheet. The microprotrusions in some of these devices are extremely small, some having dimensions (i.e., a microblade length and width) of only about 25-400 μm and a microblade thickness of only about 5-50 μm. Other penetrating elements are hollow needles having diameters of about 10 μm or less and lengths of about 50-100 μm. These tiny stratum corneum piercing/cutting elements are meant to make correspondingly small microslits/microcuts in the stratum corneum for enhanced transdermal agent delivery or transdermal body analyte sampling therethrough. The perforated skin provides improved flux for sustained agent delivery or sampling through the skin. In many instances, the microslits/microcuts in the stratum corneum have a length of less than 150 μm and a width which is substantially smaller than their length.

When microprotrusion arrays are used to improve delivery or sampling of agents through the skin, consistent, complete, and repeatable microprotrusion penetration is desired. Manual application of a skin patch including microprotrusions often results in significant variation in puncture depth across the microprotrusion array. In addition, manual application results in large variations in puncture depth between applications due to the manner in which the user applies the array. Accordingly, it would be desirable to be able to apply a microprotrusion array to the stratum corneum with an automatic device which provides microprotrusion skin piercing penetration in a consistent and repeatable manner.

Another problem with microprotrusion arrays concerns their handling by the user or a medical technician. Those microprotrusion arrays having the form of a thin, flat pad or sheet having a plurality of microprotrusions extending roughly perpendicular therefrom are especially difficult to handle manually without piercing the skin of the handler's fingers. Even if an automatic applicator is used to apply the microprotrusion array to the patient, the microprotrusion array must still be mounted on the applicator. However, during mounting or loading of the microprotrusion array onto an automatic applicator device sterility of the microprotrusions may be compromised or injury to the user may occur.

Accordingly, it would be desirable to provide a retainer for holding a microprotrusion member for connection to a reusable impact applicator device for applying the microprotrusion member to the stratum corneum.

DISCLOSURE OF THE INVENTION

The present invention relates to a retainer for holding a microprotrusion member for application of the microprotrusion member to the stratum corneum with an impact applicator. The microprotrusion member includes a plurality of microprotrusions which penetrate the stratum corneum to improve transport of an agent across the stratum corneum.

In accordance with one aspect of the present invention, a retainer for a microprotrusion member is provided. The retainer has a first end attachable to an impact applicator and a second end configured to contact the stratum corneum. A microprotrusion member having a plurality of stratum corneum piercing microprotrusions is positioned within the retainer. Preferably the microprotrusion member is positioned within the retainer in such a manner that the microprotrusions are protected from inadvertent contact by the patient or others (e.g., a medical technician) handling the retainer and/or the applicator. Most preferably, the microprotrusion member is connected to the retainer by at least one frangible element which is broken when the impact applicator is activated.

In accordance with another aspect of the present invention, a method of removably mounting a retainer onto an impact applicator adapted to impact a microprotrusion member against and pierce the stratum corneum is provided. The method includes removably fixing the retainer to the impact applicator with the microprotrusion member arranged for delivery by a piston of the impact applicator.

In accordance with an additional aspect of the invention, a retainer holding a microprotrusion array patch for application of the microprotrusion array patch to the stratum corneum by impact is provided. The retainer is preferably in the shape of a ring and a microprotrusion patch is positioned in the retainer. The microprotrusion patch includes an array of microprotrusions extending from a web. Preferably the microprotrusion member is positioned within the retainer in such a manner that the microprotrusions are protected from inadvertent contact by the patient or others (e.g., a medical technician) handling the retainer and/or the applicator. Most preferably, the microprotrusion member is connected to the retainer by at least one frangible element which is broken when impact applicator is activated.

In accordance with a further aspect of the invention, a packaged microprotrusion member and retainer assembly includes a retainer body configured to be connected to an impact applicator, a microprotrusion member mounted on the retainer body for application to the stratum corneum by impact provided by the impact applicator, and a package surrounding the retainer body and microprotrusion member.

In accordance with another aspect of the invention, a method of applying a microprotrusion member to the stratum corneum to facilitate delivery or sampling of an agent through the stratum corneum includes the steps of; (i) removing a retainer, with the microprotrusion member mounted therein, from a package, preferably a sterile package; (ii) attaching the retainer to an impact applicator, and (iii) applying the microprotrusion member to the stratum corneum with the impact applicator.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 9A shows retainer 34b with shoulder 60b at a point where the inner diameter of retainer 34b has been enlarged. This is at a point slightly below where microprotrusion member 44b has been press fit. This enlarged diameter facilitates the release of microprotrusion member 44b once it has been forced past the section of the narrow diameter.

MODES FOR CARRYING OUT THE INVENTION

An applicator system for applying a microprotrusion member as described below includes an impact applicator device for applying the microprotrusion member to the stratum corneum and a retainer for holding and protecting the microprotrusion member during storage and handling prior to impact against the skin. The retainer is shaped and configured to be mounted on the impact applicator. The retainer and microprotrusion member are preferably packaged together in an assembled condition. The retainer allows the microprotrusion member to be easily loaded on the applicator device without risk of inadvertent contact with the microprotrusions. The retainer and package also prevent contamination, folding, or other damage to the microprotrusion member prior to application, and eliminates any requirement that an operator use special techniques including hand washing, gloving, sterilized instruments, etc. when handling the microprotrusion member.

The applicator system of the present invention has particular utility in the form of a reusable impact applicator and a single use microprotrusion member. In such a configuration, the retainer is adapted to be removably mounted on the impact applicator. After the microprotrusion member has been applied to (i.e., impacted against) the skin of the patient, the now empty retainer can be removed from the applicator and subsequently a new retainer/microprotrusion member assembly mounted on the applicator. This provides cost benefits since the cost of the applicator can be spread over many microprotrusion member applications (as opposed to a single application in the case of a single use/completely disposable applicator and retainer and microprotrusion member assembly).

Figure 1:
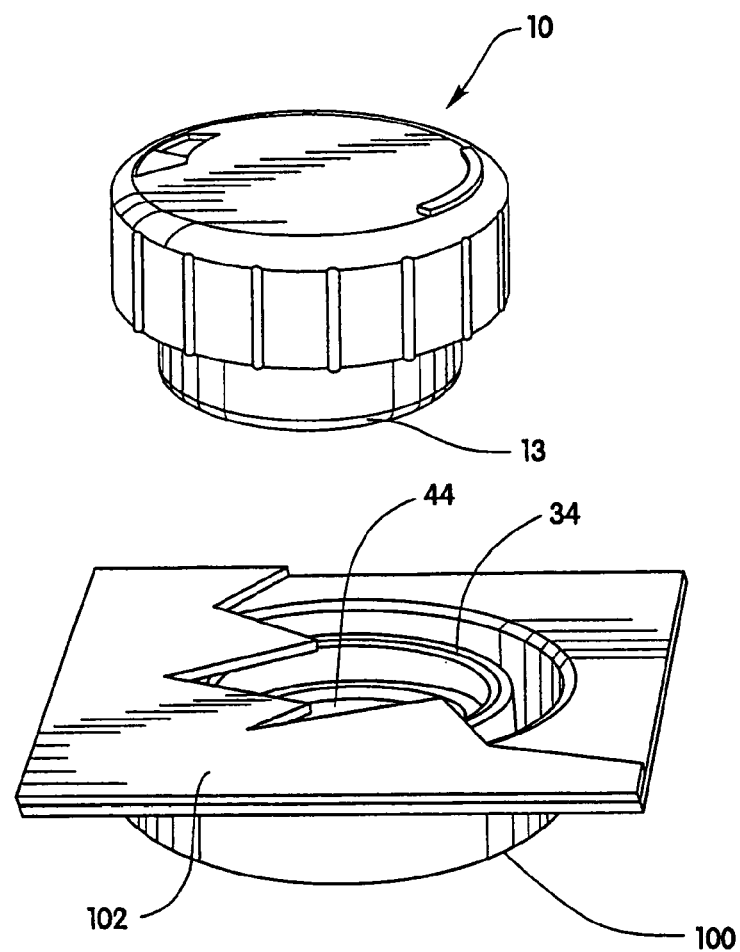
FIG. 1 is a perspective view of an applicator device and packaged retainer and microprotrusion member.

FIG. 1 illustrates a system for applying a microprotrusion member to the stratum corneum. The system includes an impact applicator 10, a retainer 34, and a microprotrusion member 44. The applicator 10 is preferably reusable while the retainer 34 and microprotrusion member 44 are preferably for one time use. As shown in FIG. 1, the retainer 34 and microprotrusion member 44 are packaged together in a preferably sterile package 100 having a removable cover 102. After removing the cover 102, a skin proximal end 13 of the applicator 10 is inserted in an open skin distal end 40 of retainer 34 in order to removably mount the retainer 34 on the applicator 10. Thus, the applicator 10 and the retainer 34 have a configuration which allows the retainer to be mounted directly onto the applicator while still in the package 100.

Figure 13:
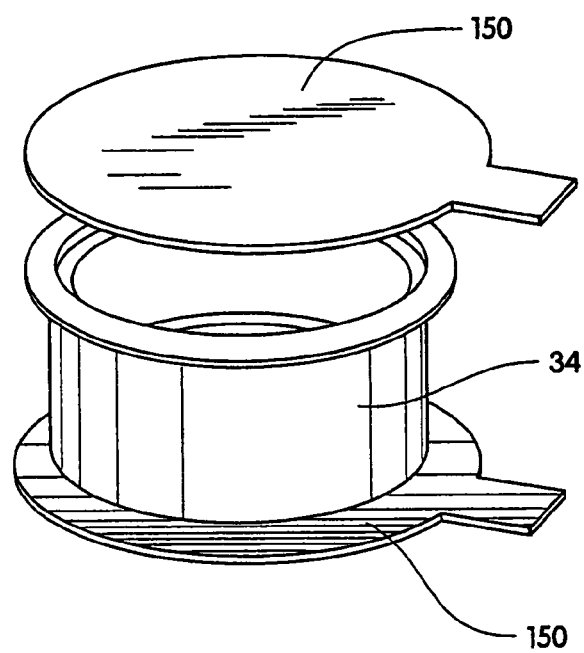
FIG. 13 is a perspective view of an alternative embodiment of a packaged retainer with releasable top and bottom peelable seals.

Alternatively, the outer housing of retainer 34 can in part act as the sealed package for microprotrusion member 44. In this embodiment the open ends of retainer 34 are sealed by removable/peelable seals 150, as shown in FIG. 13.

Figure 2:
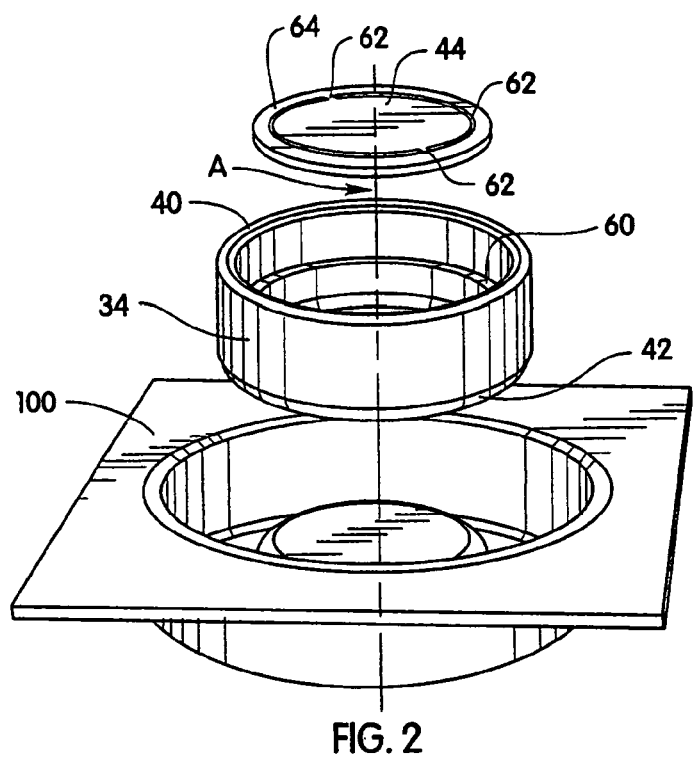
FIG. 2 is an exploded perspective view of the retainer, microprotrusion member, and package of FIG. 1.
Figure 6:
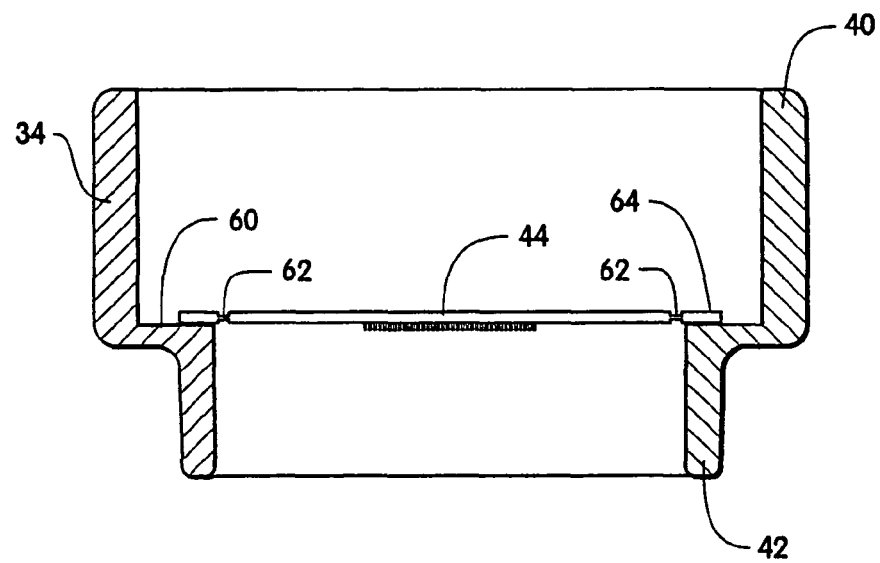
FIG. 6 is a side cross sectional view of a retainer and a microprotrusion member attached to the retainer by frangible elements.

FIG. 2 is an exploded view of the microprotrusion member 44, the retainer 34, and the package 100. The retainer 34 has a skin distal end 40 which is configured to engage the skin proximal end 14 of the applicator 10. A skin proximal end 42 of the retainer 34 provides a stratum corneum contacting surface. The retainer 34 includes a shoulder 60, positioned between ends 40 and 42, for mounting the microprotrusion member 44. The microprotrusion member 44 is connected by frangible sections 62 to a ring 64 having an adhesive coated on a skin proximal surface thereof. Though shown as a continuous circle, ring 64 could be configured instead as a plurality of discontinuous tabs spaced circumferentially around member 44. The tabs would be extensions of frangible sections 62 and partially extend peripherally about member 44, the tabs being sufficient in number and area to properly secure the tabs, member 44 and frangible sections 62 to retainer 34. The microprotrusion member is shown more clearly in FIG. 7. The ring 64 having adhesive is adhered to the shoulder 60 to secure the microprotrusion member to the retainer 34, as shown in FIG. 6. In this manner, the patch 44 is suspended in the retainer 34 and protected from unintentional contact by the user.

Figure 7:
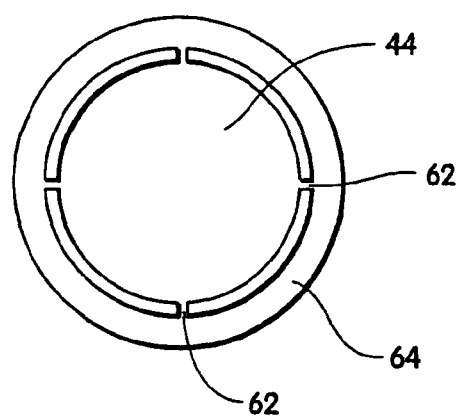
FIG. 7 is a top plan view of the microprotrusion member with frangible elements of FIG. 6.

According to one embodiment of the invention, the microprotrusion member 44 includes a base material or web or a flexible material having the microprotrusions mounted thereon. The web includes a central section having the array of microprotrusions thereon. An adhesive section of the web surrounds the central section and adheres the microprotrusion member to the stratum corneum upon application. The web also includes the frangible sections 62 surrounding the adhesive section and an outer portion or ring 64 of web material located peripherally around the frangible sections which is attached to the retainer 34. FIGS. 2 and 7 illustrate four evenly spaced frangible sections 62. However, other number and arrangements of the frangible sections 62 may be used.

Figure 8:
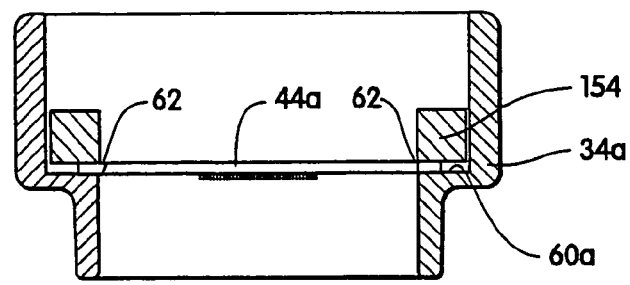
FIG. 8 is a side cross sectional view of a retainer and a microprotrusion member attached to the retainer by an interference fit.
Figure 9:
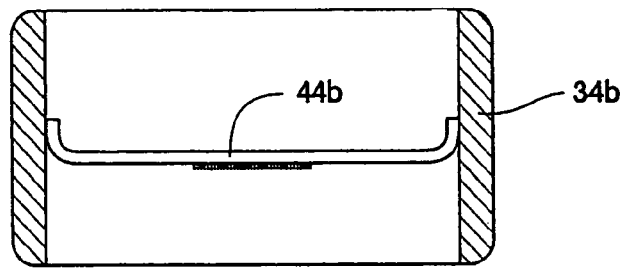
FIG. 9 and FIG. 9A are side cross sectional views of a retainer and a microprotrusion member attached to the retainer by a friction fit.
Figure 9A:
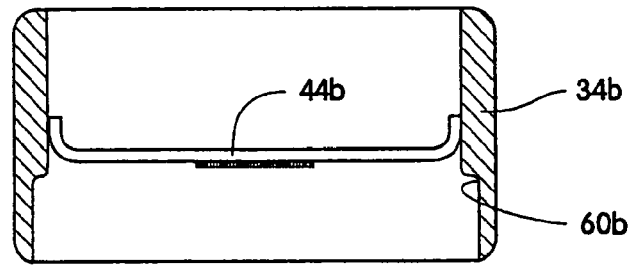
Figure 10:
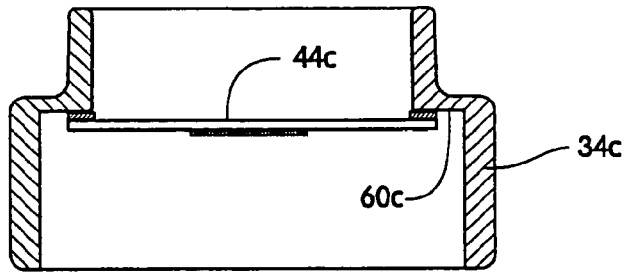
FIG. 10 is a side cross sectional view of a retainer and a microprotrusion member attached to the retainer by an adhesive.

Other releasable mounting systems for mounting the microprotrusion member 44 within the retainer 34, shown in FIGS. 8 to 10, can be used as long as the force or energy needed to release the member 44 from the retainer 34 can be adequately provided by the energy source (in applicator 10, the energy source is spring 20) in the applicator 10. Alternative means for releasably mounting microprotrusion member 44 within retainer 34 are illustrated in FIGS. 8 to 10 and include an interference fit in which the member 44 is trapped by a pressed-in ring, friction fitting the member 44 within retainer 34, and adhering member 44 within retainer 34 using an adhesive with a low bond strength.

FIG. 8 illustrates a retainer 34a having a press-in ring 154 which traps an edge of a microprotrusion member 44a between shoulder 60a and ring 154.

FIG. 9 shows a retainer 34b without a shoulder and a microprotrusion member 44b which is relatively rigid and forms a press fit within the retainer 34b.

FIG. 10 illustrates an alternative embodiment of a retainer 34c with an inverted shoulder 60c having a microprotrusion member 44c attached to the shoulder by a low bond strength adhesive which releases during application of the microprotrusion member 44c to the stratum corneum. This embodiment would require no frangible sections 62.

The manner in which the microprotrusion member 44 is mounted in the retainer 34 and the location of the patch may vary. For example, the microprotrusion member 44 may be positioned adjacent the skin proximal end 42 of the retainer 34. In addition, the microprotrusion member 44 may be secured within the retainer 34 by trapping the ring 64 between two cooperating parts of the retainer 34.

The retainer 34 is preferably attached to the applicator 10 after cocking of the piston 14. The retainer 34 can be attached by a snap in connection requiring less force to snap in than the force required to release the piston.

Figure 14:
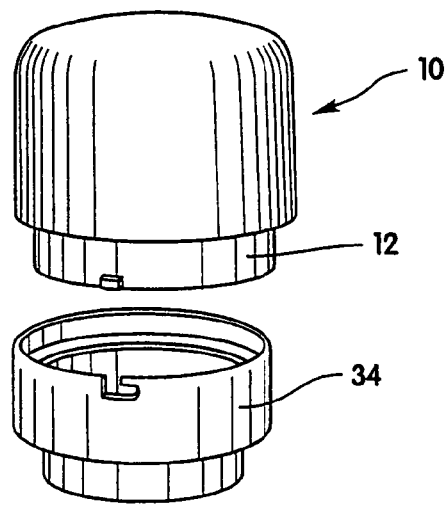
FIG. 14 is a perspective view of an applicator and retainer attachable to the applicator by a bayonet fitting.
Figure 15:
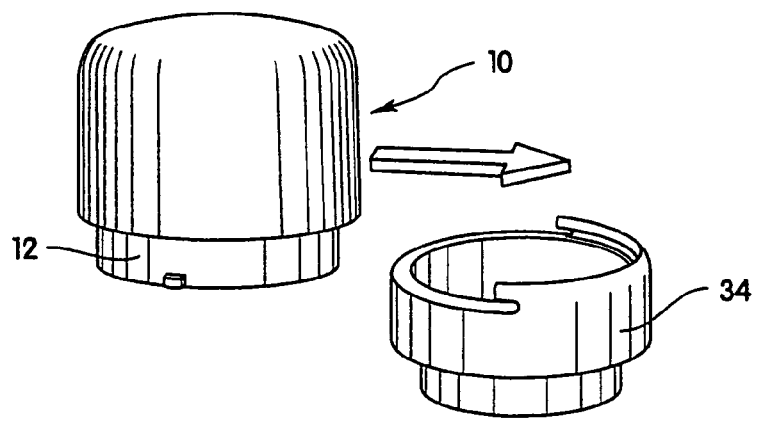
FIG. 15 is a perspective view of an applicator and retainer attachable to the applicator by a slide-on fitting.

The retainer 34 may also be attached to the applicator 10 by a bayonet fitting (FIG. 14) which allows retainer 34 to twist onto the applicator body. Another to attached retainer 34 is a slide on fitting (FIG. 15) which allows retainer 34 to slide onto the applicator body 12 in a direction normal to the axis of the applicator.

Figure 16:
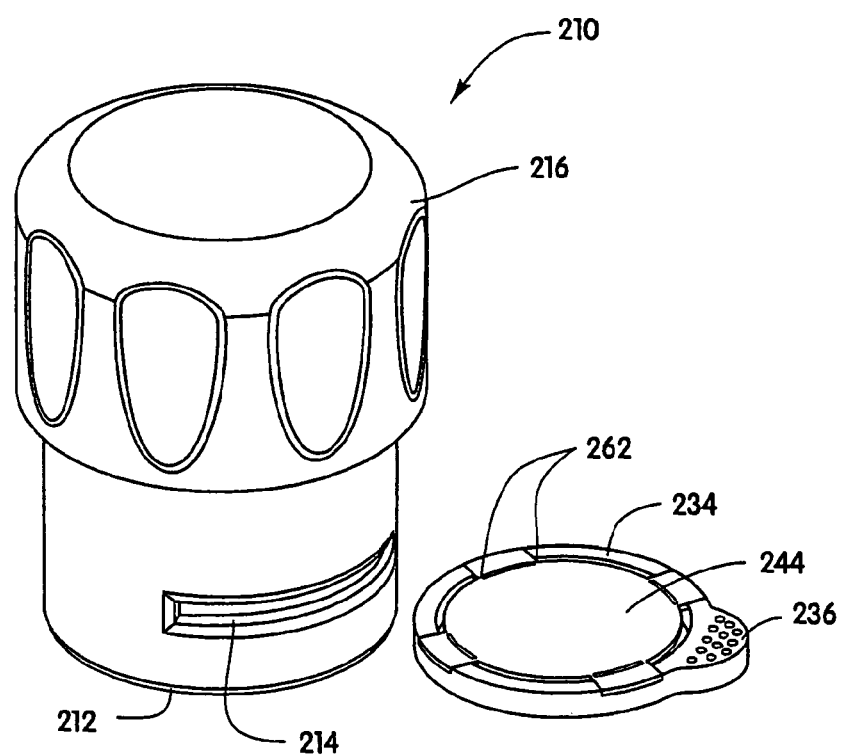
FIG. 16 is a perspective view of an applicator and retainer adapted to be inserted into a slot in the applicator.

Yet another way of mounting the retainer within the applicator is illustrated in FIG. 16. FIG. 16 illustrates another embodiment of a hand operated spring-loaded applicator having an end 212 adapted to contact the skin of the patient. Adjacent to end 212 is a slot 214 through which the retainer 234 can be inserted. Like retainer 34, retainer 234 also has a ring-shaped configuration. Mounted within the retainer 234 is a microprotrusion member 244, which is connected to retainer 234 by a plurality of frangible connects 262 which are connected to a plurality of tabs 264. Tabs 264 are coated with adhesive on the skin proximal side which facilitates the attachment of tabs 264 to retainer 234. A finger grip 236 is preferably provided in one section of retainer 234 in order to provide a convenient place for grasping retainer 234 and to help prevent inadvertent contact between the user's fingers and the microprotrusions in member 244. After inserting the retainer 234 into slot 214, the user places edge 212 against the skin surface to be treated. Then, cap 216 is pressed towards the skin causing the piston (not shown) to be released and impact the microprotrusion member 244 against the skin.

In order to apply a microprotrusion member 44 according to the present invention, the package 100 of FIG. 1 is opened by removing the releasable film cover 102. Then, the retainer 34 is attached to the applicator 10. An outside surface of the retainer 34 can be handled without contacting the microprotrusion member 44. Thus, contamination of the microprotrusion member 44 and inadvertent exposure of the physician, nurse, medical technician or even the patient to the microprotrusions and any drugs contained thereon, are prevented. The applicator device 10 with the retainer 34 mounted thereon is then ready for use to pierce the stratum corneum. The skin proximal end 42 of the retainer 34 is placed against the stratum corneum and pressed down with a force which causes piston 14 of the applicator to be released. The microprotrusion member 44 is separated from the retainer 34 by the downward force of the piston 14 which fractures the frangible sections 62.

Figure 3:
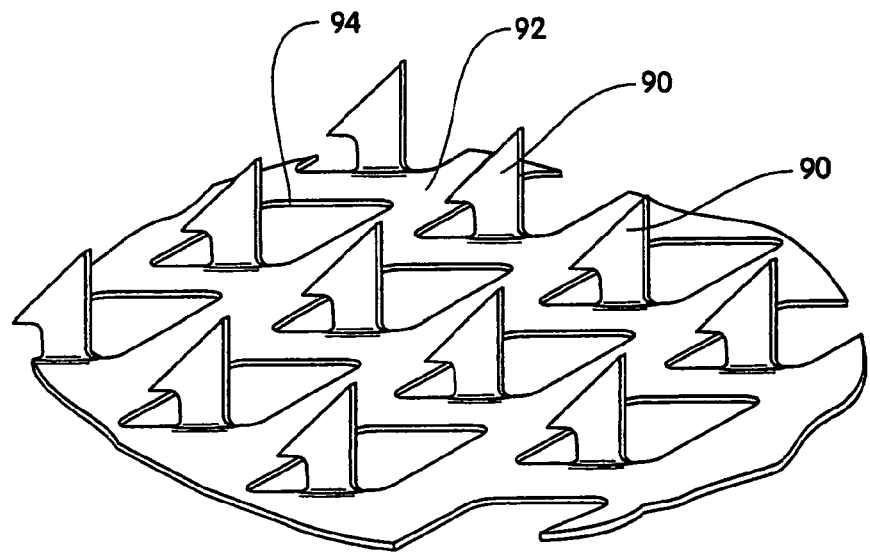
FIG. 3 is a perspective view of a portion of one example of a microprotrusion member.

FIG. 3 illustrates one embodiment of a microprotrusion member for use with the present invention. FIG. 3 shows a plurality of microprotrusions in the form of microblades 90. The microblades 90 extend at a substantially 90° angle from a sheet 92 having openings 94. The sheet 92 may be incorporated in an agent delivery patch or an agent sampling patch which includes an agent reservoir and/or an adhesive for adhering the patch to the stratum corneum. Examples of agent delivery and sampling patches which incorporate a microprotrusion array are found in WO 97/48440, WO 97/48441, WO 97/48442, the disclosures of which are incorporated herein by reference. The microprotrusion array of FIG. 3 without a reservoir may also be applied alone as a skin pretreatment.

The term "microprotrusion" as used herein refers to very tiny stratum corneum piercing elements typically having a length of about 10-500 µm, and preferably about 50-400 µm, which make a penetration in the stratum corneum. In order to penetrate the stratum corneum, the microprotrusions preferably have a length of at least 10 µm, more preferably at least 50 µm. The microprotrusions may be formed in different shapes, such as needles, hollow needles, blades, pins, punches, and combinations thereof.

The term "microprotrusion array" as used herein refers to a plurality of microprotrusions arranged in an array for piercing the stratum corneum. The microprotrusion array may be formed by cutting a plurality of blades from a thin sheet and folding each of the blades out of the plane of the sheet to form the configuration shown in FIG. 3. The microprotrusion array may also be formed in other known manners, such as by connecting multiple strips having microprotrusions along an edge of each of the strips. The microprotrusion array may include hollow needles, for example hollow needles adapted to inject a liquid formulation.

Examples of microprotrusion arrays and methods of making same are described in U.S. Pat. No. 5,879,326 issued to Godshall, et al., U.S. Pat. No. 3,814,097 issued to Ganderton, et al., U.S. Pat. No. 5,279,544 issued to Gross, et al., U.S. Pat. No. 5,250,023 issued to Lee, et al., U.S. Pat. No. 3,964,482 issued to Gerstel, et al., Reissue 25,637 issued to Kravitz, et al., and PCT Publication Nos. WO 96/37155, WO 96/37256, WO 96/17648, WO 97/03718, WO 98/11937, WO 98/00193, WO 97/48440, WO 97/48441, WO 97/48442, WO 98/00193, WO 99/64580, WO 98/28037, WO 98/29298, and WO 98/29365, all of which are incorporated herein by reference in their entirety.

Figure 4:
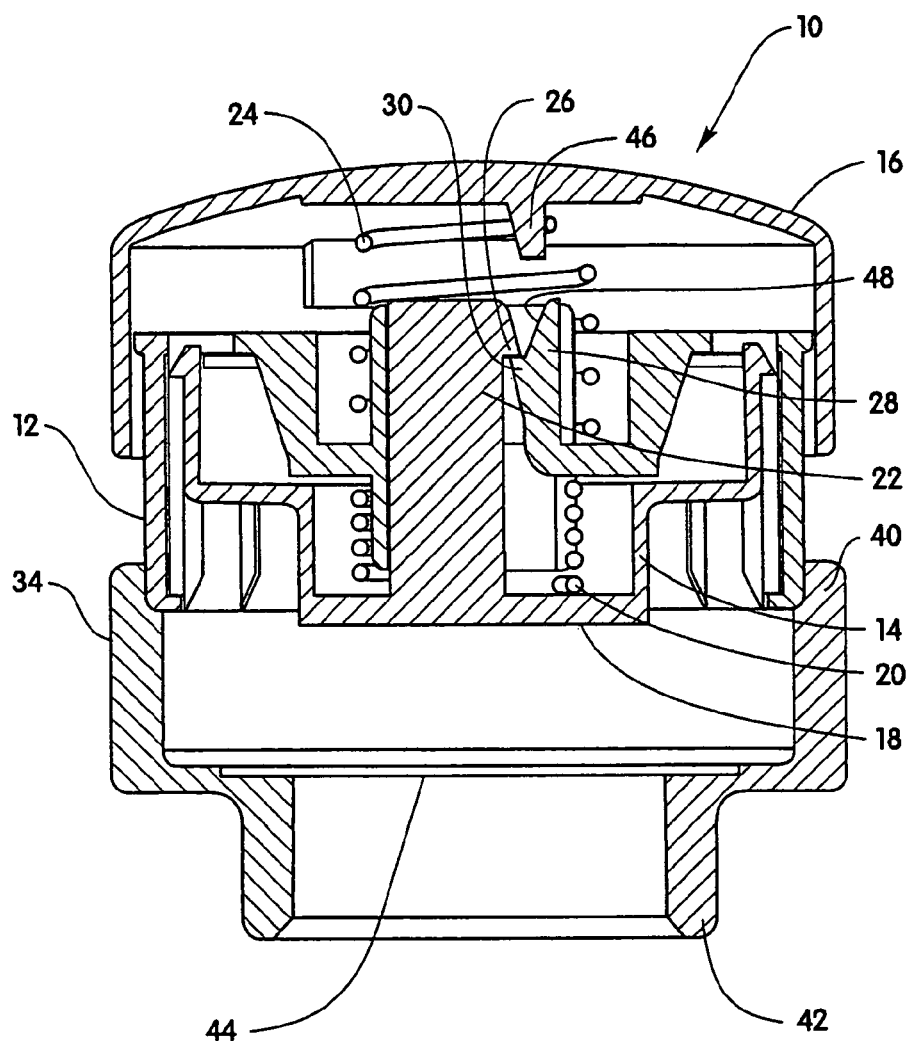
FIG. 4 is a side cross sectional view of an applicator device in a cocked position with a retainer and microprotrusion member attached to the applicator.
Figure 5:
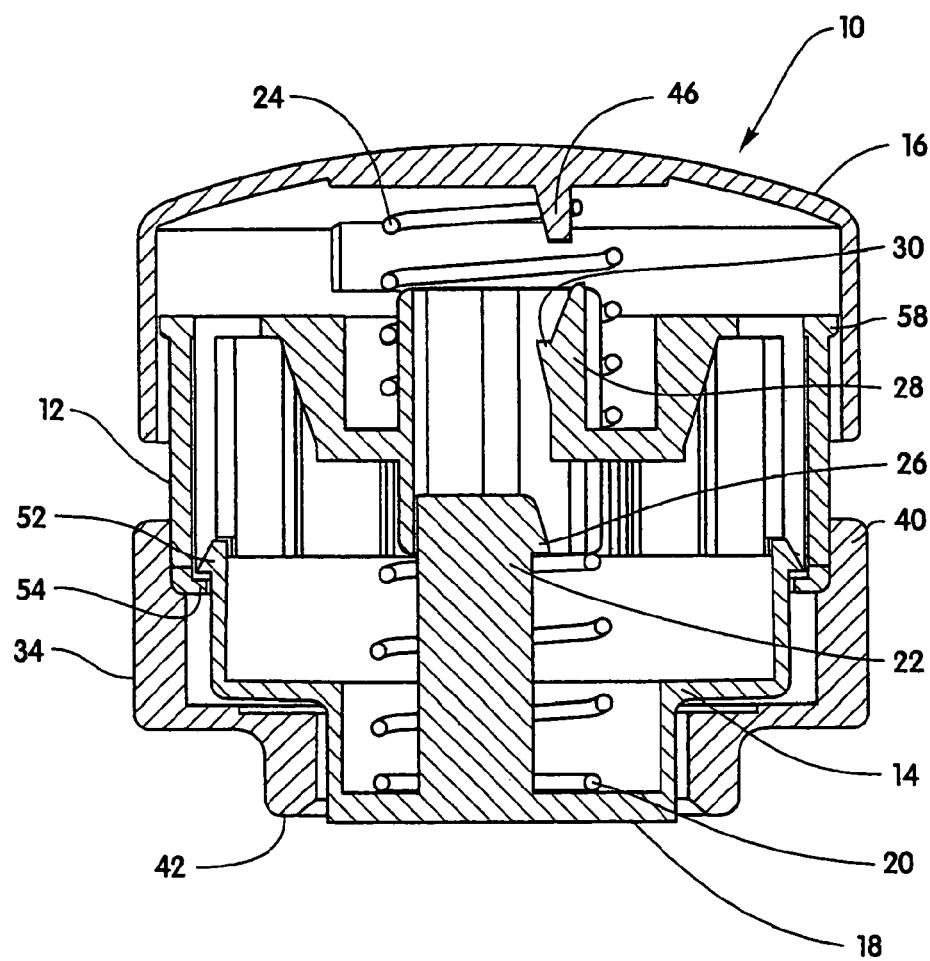
FIG. 5 is a side cross sectional view of the applicator device of FIG. 4 after the piston has been released to impact and apply to the skin, the microprotrusion member.

FIGS. 4 and 5 illustrate one exemplary embodiment of an applicator 10 for use with the retainer 34 of the present invention. However, other applicator configurations may also be used with the retainers which are described herein.

The applicator 10 includes a body 12 and a piston 14 movable within the body. A cap 16 is provided on the body 12 for activating the applicator to impact the stratum corneum with the microprotrusion member 44. An impact spring 20 is positioned around a post 22 of the piston 14 and biases the piston downward (i.e., towards the skin) with respect to the body 12. The piston 14 has an impact surface 18 which is substantially planar, slightly convex, or configured to match the contours of a particular body surface. The surface 18 of the piston 14 impacts the microprotrusion member 44 against the skin causing the microprotrusions 90 to pierce the stratum corneum.

FIG. 4 shows the piston 14 in the cocked position. When the applicator is cocked, the piston 14 is pressed up inside the body 12 and locked in place by a locking mechanism. The locking mechanism includes a stop 26 on the post 22 and a flexible finger 28 on the body 12 having a corresponding stop 30. As the piston 14 is moved toward the body 12 compressing the impact spring 20, the stop 26 flexes the finger 28 and snaps over the corresponding stop 30 of the flexible finger. The cocking step is performed by a single compression motion which both cocks and locks the piston 14 in the cocked position.

As shown in FIG. 4, in the cocked position, catch 26 and latch 30 on the piston 14 and body 12 are releasably engaged, preventing downward motion of the piston in the body. FIG. 4 also illustrates the patch retainer 34 mounted on the body 12.

The applicator 10 has been described for use with a microprotrusion member 44. The microprotrusion member 44 may be a patch which generally includes a microprotrusion array, an agent reservoir, and a backing. However, the applicator 10 may also be used with a microprotrusion member 44 without an agent reservoir. In this case, the microprotrusion member is used as a pretreatment which is followed by the application of an agent with a separate device. Alternatively, the microprotrusion member 44 may incorporate the agent as a coating on the microprotrusion array, e.g. for delivering a vaccine intradermally.

The activation of the applicator 10 by releasing the locking mechanism is performed by downward force applied to the applicator cap 16 while the end 42 of the applicator is held against the skin. The cap 16 is biased in a direction away from the skin by a hold down spring 24 which is positioned between the body 12 and the cap. The cap 16 includes a pin 46 extending downward from the cap. When the cap 16 is pressed downward against the bias of the hold down spring 24, the pin 46 contacts ramp 48 on flexible finger 28 moving the flexible finger outward and disengaging latch 30 of the flexible finger 28 from catch 26. This releases piston 14 and the piston moves downward impacting the stratum corneum with the microprotrusion member 44. The impact is applied substantially parallel to a central axis of the microprotrusion member 44.

FIG. 5 illustrates the applicator 10 after the device has been activated and a microprotrusion member 44 has been applied to the stratum corneum. The hold down spring 24 is selected such that a predetermined hold down force must be achieved before the device is activated. The hold down force causes the stratum corneum to be stretched by the surface 42 of the retainer 34 so that the skin is under optimal tension at the time the microprotrusion member 44 impacts the skin. The hold down force applied by the hold down spring 24 is preferably selected to cause the surface 42 to apply a tension to the skin in the range of about 0.01 to 10 megapascals (MPa), more preferably about 0.05 to 2 MPa.

A balance between the hold down spring 24 and the impact spring 20 allows the cocking of the piston 14 by pressing on the cap 16 without causing the finger 46 to release the locking mechanism. The impact spring 20 is selected to achieve a predetermined impact which is appropriate for a particular patch to provide the desired microprotrusion penetration. In general, the microprotrusion member 44 is impacted against human skin with a power of at least 0.05 joules per $cm^2$ in 10 msec or less, preferably with power of at least 0.1 joules per $cm^2$ of microprotrusion member in 1 msec or less.

The applicator 10 according to the present invention has been described with respect to an orientation in which the skin proximal side of the device is shown at the bottom of the figures. It should be understood that the applicator device may be used in other orientations (e.g., sideways or upside down) from that shown in the figures.

Figure 11:
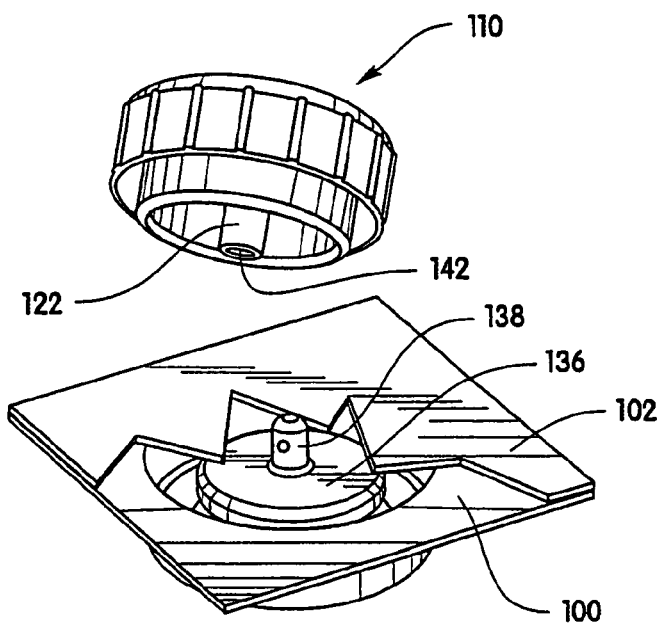
FIG. 11 is a perspective view of an applicator device and packaged retainer and microprotrusion member according to a second embodiment of the invention.
Figure 12:
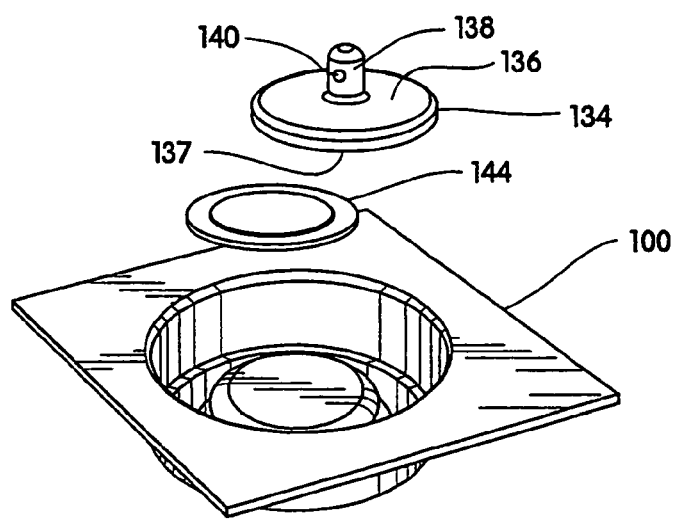
FIG. 12 is an exploded perspective view of the retainer, microprotrusion member, and package of FIG. 11.

FIGS. 11 and 12 illustrate an alternative embodiment of the invention including a retainer 134 which is releasably mounted on a piston 122 of the impact applicator 110. The retainer 134 includes a disk shaped head 136 and a shaft 138. The shaft 138 includes a detent 140 or projection which allows the shaft to snap into a corresponding recess 142 in piston 122 of the applicator 110. The disk shaped head 136 has a microprotrusion member application surface 137 with the microprotrusion member releasably fixed to the application surface 137 by adhesive or other means. If adhesive is used to fix the microprotrusion member 144 to the retainer 134, the adhesive used holds the microprotrusion member less securely than an adhesive which secures the microprotrusion member 144 to the skin. A package 100 avoids damage to the microprotrusion member 144 during shipping and storage and also can serve the function of a release liner.

In order to apply a microprotrusion member 144 according to the embodiment of FIGS. 11 and 12, the package 100 is opened by removing the releasable film cover 102. Then the retainer 134 is attached to the applicator device 110 by inserting the shaft 138 into the recess 142 in the applicator device 110. The package 100 is then removed leaving retainer 134 releasably engaged to applicator device 110. Applicator device 110 is now ready for application of the microprotrusion member 144 to the stratum corneum. The microprotrusion member 144 is then applied to the stratum corneum by the impact applicator device 110. The applicator device 110 and the attached retainer 134 are moved away from the stratum corneum leaving the microprotrusion member 144 impacted on the stratum corneum.

The device of the present invention can be used in connection with agent delivery, agent sampling, or both. In particular, the device of the present invention is used in connection with transdermal drug delivery, transdermal analyte sampling, or both. Transdermal delivery devices for use with the present invention include, but are not limited to passive devices, osmotic devices, pressure-driven devices, and electrotransport devices. Transdermal sampling devices for use with the present invention include, but are not limited to, passive devices, negative pressure driven devices, osmotic devices, and reverse electrotransport devices. The transdermal devices of the present invention may be used in combination with other methods of increasing agent flux, such as skin permeation enhancers.

The device of the present invention may be used with a microprotrusion array included in a transdermal delivery or sampling patch having adhesive for attaching the patch to the skin. Alternatively, the microprotrusion member and delivery or sampling patch may be two separate elements with the microprotrusion member used for pretreatment prior to application of the delivery or sampling patch.

While the invention has been described in detail with reference to the preferred embodiments thereof, it will be apparent to one skilled in the art that various changes and modifications can be made and equivalents employed, without departing from the present invention.

The invention claimed is:

1. A method of applying a microprotrusion member to the stratum corneum to facilitate transdermal delivery of an agent, the method comprising the steps of:
   providing a reusable applicator device adapted to apply said microprotrusion member;
   providing a single use retainer releasably securing said microprotrusion member,
      wherein said retainer is adapted to be removably mounted on the impact applicator;
   attaching said retainer to said applicator device;
   placing said retainer and applicator device assembly on a desired site on the stratum corneum; and
   applying a hold down force to the stratum corneum with said retainer and applicator device assembly, whereby a tensile force is applied to said stratum corneum site in the range of approximately 0.01-10 MPa and whereby upon application of said hold down force said applicator device activates and applies said microprotrusion member to the stratum corneum,
      wherein said microprotrusion member is released from said retainer after application, resulting in an empty retainer.

2. A method of applying a microprotrusion member to the stratum corneum to facilitate transdermal delivery of an agent, the method comprising the steps of:
   providing a reusable impact applicator device;
   providing a single use retainer releasably securing said microprotrusion member,
      wherein said retainer is adapted to be removably mounted on the impact applicator;
   attaching said retainer to said applicator device; and
   applying said microprotrusion member to the stratum corneum with said impact applicator, said applicator being adapted to activate upon application of a hold down force to the stratum corneum with said retainer and applicator device assembly
   said hold down force being sufficient to apply a tensile force to the stratum corneum in the range of approximately 0.01-10 MPa, said applicator device being further adapted to apply said microprotrusion member to the stratum corneum with a power of at least 0.05 joules per $cm^2$ in 10 msec. or less,
      wherein said microprotrusion member is released from said retainer after application, resulting in an empty retainer.

* * * * *